United States Patent [19]
Huang et al.

[11] Patent Number: 5,817,688
[45] Date of Patent: Oct. 6, 1998

[54] PESTICIDAL 1-ARYLPYRAZOLE DERIVATIVES

[75] Inventors: Jamin Huang, Chapel Hill; Patrick Doyle Lowder; Nicholas Charles Ray, both of Raleigh, all of N.C.; David W. Hawkins, Ongar, England

[73] Assignee: Rhone-Poulenc Inc., Research Triangle Park, N.C.

[21] Appl. No.: 761,982

[22] Filed: Dec. 11, 1996

Related U.S. Application Data

[60] Provisional application Nos. 60/008,869 Dec. 19, 1995 and 60/028,520 Oct. 18, 1996.

[51] Int. Cl.$^6$ ............ A01N 43/56; C07D 231/18
[52] U.S. Cl. ............ 514/407; 548/369.4
[58] Field of Search ............ 548/369.4; 514/407

[56] References Cited

U.S. PATENT DOCUMENTS

| | | |
|---|---|---|
| 4,614,533 | 9/1986 | Schallner et al. . |
| 4,746,354 | 5/1988 | Gehring et al. . |
| 4,752,326 | 6/1988 | Ohyama et al. . |
| 4,772,312 | 9/1988 | Schallner et al. . |
| 4,804,675 | 2/1989 | Jensen-Korte et al. . |
| 4,810,720 | 3/1989 | Jensen Korte et al. . |
| 5,232,940 | 8/1993 | Hatton et al. . |
| 5,306,694 | 4/1994 | Phillips et al. . |
| 5,547,974 | 8/1996 | Hattou et al. ............ 548/369.4 |
| 5,712,303 | 1/1998 | Faraei et al. ............ 548/369.4 |

FOREIGN PATENT DOCUMENTS

| | | |
|---|---|---|
| 0202169 | 11/1986 | European Pat. Off. . |
| 0302327 | 2/1989 | European Pat. Off. . |
| 0382034 | 8/1990 | European Pat. Off. . |
| 0398499 | 11/1990 | European Pat. Off. . |
| 0588105 | 3/1994 | European Pat. Off. . |
| 2701091 | 7/1977 | Germany . |
| 3509567 | 9/1986 | Germany . |
| 3600287 | 7/1987 | Germany . |
| 3711928 | 10/1988 | Germany . |

OTHER PUBLICATIONS

*Comprehensive Organic Transformations,* VCH Publishers, 1989, R.C. Larock, pp. 595–596.
Doyle et al, *J. Org. Chem.,* 1977 42 (14), pp. 2431–2436.
*Protective Groups in Organic Synthesis,* 2nd ed., Wiley–Interscience, 1991, T.W. Greene and P.G.M. Wuts, pp. 175–220.
Torii et al, *Chem. Lett.,* 1984, pp. 897–898.
Soga et al, *Bull. Chem. Soc. Jpn.,* 1990, 63, pp. 3122–3131.
*Comprehensive Organic Transformations,* VCH Publishers, 1989, R.C. Larock, pp. 604–614.
*Advanced Organic Chemistry,* 4th ed., J. Wiley and Sons, 1992, Mar., pp. 804–806.
*Modern Organic Chemistry,* 2nd ed. Benjamin Cummings, 1972, H.O. House, p. 763.
Bauer et al, *Journal of Fluorine Chemistry,* 16 (1980), pp. 129–136.

Primary Examiner—Robert W. Ramsuer
Attorney, Agent, or Firm—Burns, Doane, Swecker & Mathis, L.L.P.

[57] ABSTRACT

The invention relates to novel arylpyrazoles of the formula (I):

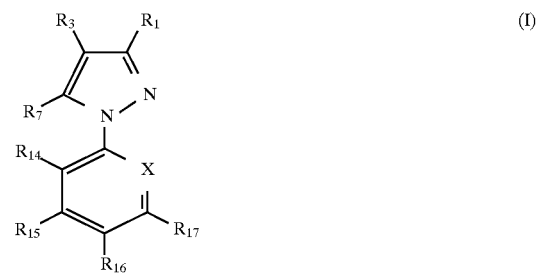

wherein $R_1$, $R_3$, $R_7$, $R_{14}$, $R_{15}$, $R_{16}$, and $R_{17}$ are as defined in the description, and to their use as pesticides.

16 Claims, No Drawings

PESTICIDAL 1-ARYLPYRAZOLE DERIVATIVES

CROSS-REFERENCE TO RELATED APPLICATIONS

This application claims the priority of U.S. Provisional Patent Applications No. 60/008,869, filed Dec. 19, 1995 and No. 60/028,520, filed Oct. 18, 1996, both of which are incorporated by reference herein in their entireties and relied upon.

The present invention relates to novel arylpyrazoles, compositions containing them, processes for their preparation, and their uses as insecticides and nematicides.

This invention relates to 1-arylpyrazole derivatives, to compositions containing them and to the use of said compounds and compositions against arthropods, particularly insects and nematodes.

U.S. Pat. No. 5,232,940 describes N-phenylpyrazoles with, among others, 5-cycloalkylcarbonyl and 5-alkoxycarbonyl substituents.

DE 3509567 and EP 382034 describe 3-nitro-1-phenylpyrazoles as herbicides and insecticides.

DE 2701091 describes fungicidal pyrazoles with amides at positions 4 or 5.

EP 202169 describes 1-(4-alkoxy)phenyl pyrazoles as herbicides.

EP 398499 describes cyano-phenylpyrazoles as insecticides.

None of the foregoing publications describes or suggests that compounds of formula (I) possess or would be expected to possess activity against arthropods, especially insects or nematodes.

This invention provides novel arylpyrazoles of the formula (I):

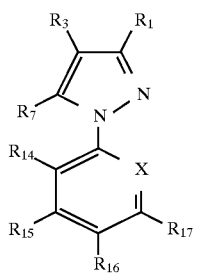

wherein:

$R_1$ is selected from cyano, halogen, formyl, $C(O)R_2$, H, and $R_2$;

$R_2$ is selected from $C_1$–$C_4$ alkyl, $C_1$–$C_4$ haloalkyl, and cycloalkyl optionally substituted with one or more halogens;

$R_3$ is selected from halogen, $C_1$–$C_4$ alkyl, $C_1$–$C_4$ haloalkyl, nitro, $CONR_4R_5$, $COOR_4$, and $—S(O)_nR_6$;

$R_4$ and $R_5$ are independently selected from H, $C_1$–$C_5$ alkyl, and $C_1$–$C_5$ haloalkyl;

$R_6$ is selected from $C_1$–$C_4$ alkyl, $C_1$–$C_4$ haloalkyl, and cycloalkyl optionally substituted with one or more halogens;

$R_7$ is selected from $C(O)R_8$, $C_1$–$C_6$ α-hydroxyalkyl, $C_1$–$C_6$ α-hydroxyhaloalkyl, $C(OR_9)=CHR_{10}$, $CHR_{11}R_{12}$, $—CR_{13}=ND$ and

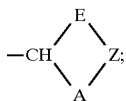

$R_8$ is selected from H, $C_1$–$C_5$ alkyl, and $C_1$–$C_5$ haloalkyl;

$R_9$ is selected from $C(O)R_{18}$, CHO, $—S(O)_2R_{18}$, $—S(O)_2$aryl, $C_3$–$C_{18}$ trialkylsilyl, $C_8$–$C_{18}$ dialkylarylsilyl, $C_{13}$–$C_{20}$ diarylalkylsilyl and $C_{18}$–$C_{24}$ triarylsilyl;

$R_{10}$ is selected from H, $C_1$–$C_4$ alkyl, and $C_1$–$C_4$ haloalkyl;

$R_{11}$ and $R_{12}$ are independently selected from $C_1$–$C_4$ alkoxy, $C_1$–$C_4$ haloalkoxy, $C_1$–$C_4$ alkylthio, $C_1$–$C_4$ haloalkylthio, $NR_8R_{10}$, $C_3$–$C_8$ trialkylsiloxy and cyano;

$R_{13}$ is selected from H, $C_1$–$C_5$ alkyl, and $C_1$–$C_5$ haloalkyl;

$R_{14}$ is selected from H, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, cyano and nitro;

$R_{15}$ and $R_{17}$ are independently selected from H and halogen;

$R_{16}$ is selected from halogen, $C_1$–$C_4$ alkyl, $C_1$–$C_4$ haloalkyl, $C_1$–$C_4$ alkoxy, $C_1$–$C_4$ haloalkoxy, cyano, nitro, $C(O)R_{18}$, and $—S(O)_qR_{19}$;

$R_{18}$ is selected from $C_1$–$C_3$ alkyl and $C_1$–$C_3$ haloalkyl;

$R_{19}$ is selected from $C_1$–$C_3$ alkyl and $C_1$–$C_3$ haloalkyl;

X is selected from a nitrogen atom or $C—R_{20}$;

$R_{20}$ is selected from H, halogen, cyano, nitro, $C_1$–$C_4$ alkyl, $C_1$–$C_4$ haloalkyl, $C_1$–$C_4$ alkoxy, and $C_1$–$C_4$ haloalkoxy;

A and E are independently selected from $NR_{21}$, O and S;

$R_{21}$ is selected from H, $C_1$–$C_4$ alkyl and $C_1$–$C_4$ haloalkyl;

D is selected from $OR_{22}$ and $NR_{23}R_{24}$;

$R_{22}$, $R_{23}$ and $R_{24}$ are independently selected from H, $C_1$–$C_4$ alkyl, and $C_1$–$C_4$ haloalkyl;

Z is $(CH_2)_m$;

m is 2, 3 or 4;

n is 0, 1 or 2;

q is 0, 1 or 2;

and pesticidally acceptable salts thereof;

provided that:

$R_{11}$ and $R_{12}$ are always the same except when $R_{12}$ is cyano; and $R_4$ is not H when $R_3$ is $COOR_4$.

By the term "pesticidally acceptable salts" is meant salts the anions of which are known and accepted in the art for the formation of pesticidally acceptable salts. Preferably such salts are water soluble. Suitable acid addition salts, formed by compounds of formula (I) containing an amine group, include salts with inorganic acids, for example hydrochlorides, phosphates, sulfates, nitrates; and salts with organic acids, for example acetates.

In this specification, "halogen" means the atoms fluorine, chlorine, bromine and iodine. Alkyl groups and moieties may be either linear or branched chain. "Cycloalkyl" means a cycloalkyl group having from three to seven carbon atoms in the ring, each of which optionally bears one or more $C_1$–$C_4$ alkyl. "Aryl" means phenyl optionally substituted by one or more of the members of the group consisting of $C_1$–$C_4$ alkyl and halogen which may be the same or different. It will be understood that in certain cases, compounds of formula (I) can be present in the form of optical and/or stereoisomers. All such forms are embraced by the invention.

Compounds of formula (I) above in which $R_7$ is formyl generally possess a lower level of activity as insecticides but are useful as intermediates in the preparation of more highly active species.

It will be understood that the provisos appearing in the above description are present for reasons of biological efficacy and synthetic accessibility.

A feature of the invention are those compounds having one or more of the following features:

$R_1$ is cyano;
$R_3$ is $-S(O)_nR_6$;
$R_7$ is selected from the group $C(O)R_8$, $C_1-C_6$ α-hydroxyalkyl, $C_1-C_6$ α-hydroxyhaloalkyl, $C(OR_9)=CHR_{10}$, $CHR_{11}R_{12}$, and $-CR_{13}=ND$;
$R_{14}$ is halogen;
$R_{15}$ and $R_{17}$ are H;
$R_{16}$ is $C_1-C_4$ haloalkyl; and
X is C—$R_{20}$.

Preferred compounds of formula (I) above are compounds wherein:

$R_1$ is selected from cyano, halogen, $C(O)R_2$, H, and $R_2$;
$R_3$ is $-S(O)_nR_6$;
$R_7$ is selected from $C(O)R_8$, $-CR_{13}=ND$, and $-CHR_{11}R_{12}$;
$R_{14}$ is halogen;
$R_{15}$ and $R_{17}$ are H; and
$R_{16}$ is $C_1-C_4$ haloalkyl.

A further preferred class of compounds of formula (I) are those wherein:

$R_1$ is cyano;
$R_3$ is $-S(O)_nR_6$;
$R_6$ is $C_1-C_2$ haloalkyl, preferably $CF_3$;
$R_7$ is selected from $C(O)R_8$, $-CHR_{11}R_{12}$ and $-CR_{13}=ND$;
$R_{11}$, is $C_1-C_4$ alkoxy;
$R_{12}$ is selected from $C_1-C_4$ alkoxy and cyano;
$R_{14}$ is halogen;
$R_{15}$ and $R_{17}$ are H;
$R_{16}$ is $C_1-C_2$ haloalkyl, especially $CF_3$.

The numbers 1–21 are assigned to these compounds for reference and identification. Hereinafter compounds of formula (I) include the following:

1. 5-Acetyl-3-cyano-1-(2,6-dichloro-4-trifluoromethylphenyl)-4-trifluoromethylsulfonylpyrazole, m.p. about 161° C.;
2. 3-Cyano-1-(2,6-dichloro-4-trifluoromethylphenyl)-5-formyl-4-trifluoromethylthiopyrazole, m.p. about 90° C.;
3. 5-{(N-amino)iminomethylidenyl}-3-cyano-1-(2,6-dichloro-4-trifluoromethylphenyl)-4-trifluoromethylthiopyrazole, m.p. about 130° C.;
4. 3-Cyano-1-(2,6-dichloro-4-trifluoromethylphenyl)-5-dimethoxymethyl-4-trifluoromethylthiopyrazole, m.p. about 93° C.;
5. 3-Cyano-1-(2,6-dichloro-4-trifluoromethylphenyl)-5-{(N-methoxy)iminomethylidenyl}-4-trifluoromethylthiopyrazole, m.p. about 87° C.;
6. 3-Cyano-5-{(1-cyano-1-methoxy)methyl}-1-(2,6-dichloro-4-trifluoromethylphenyl)-4-trifluoromethylthiopyrazole, an oil;
7. 3-Cyano-1-(2,6-dichloro-4-trifluoromethylphenyl)-5-(hydroxy)methyl-4-trifluoromethylthiopyrazole, m.p. about 118° C.;
8. 3-Cyano-1-(2,6-dichloro-4-trifluoromethylphenyl)-5-(1-hydroxy)ethyl-4-trifluoromethylthiopyrazole, m.p. about 123° C.;
9. 5-Acetyl-3-cyano-1-(2,6-dichloro-4-trifluoromethylphenyl)-4-trifluoromethylthiopyrazole, m.p. about 128° C.;
10. 5-Acetyl-3-cyano-1-(2,6-dichloro-4-trifluoromethylphenyl)-4-trifluoromethylsulfinylpyrazole, m.p. 156° C.;
11. 3-Cyano-1-(2,6-dichloro-4-trifluoromethylphenyl)-5-(N,N-dimethylaminoiminomethylidenyl)-4-trifluoromethylthiopyrazole, m.p. about 126° C.;
12. 3-Cyano-1-(2,6-dichloro-4-trifluoromethylphenyl)-5-(hydroxy)methyl-4-trifluoromethylsulfinylpyrazole, m.p. about 153° C.;
13. 3-Cyano-1-(2,6-dichloro-4-trifluoromethylphenyl)-5-dimethoxymethyl-4-trifluoromethylsulfinylpyrazole, m.p. about 116° C.;
14. 3-Cyano-5-{(1-cyano-1-methoxy)methyl}-1-(2,6-dichloro-4-trifluoromethylphenyl)-4-trifluoromethylsulfinylpyrazole, m.p. about 167° C.;
15. 3-Cyano-1-(2,6-dichloro-4-trifluoromethylphenyl)-5-dimethoxymethyl-4-trifluoromethylsulfonylpyrazole, m.p. 137° C.;
16. 3-Cyano-5-{(1-cyano-1-methoxy)methyl}-1-(2,6-dichloro-4-trifluoromethylphenyl)-4-trifluoromethylsulfonylpyrazole, m.p. 90° C.;
17. 3-Cyano-1-(2,6-dichloro-4-trifluoromethylphenyl)-5-(1-hydroxy-2,2,2-trifluoroethyl)-4-trifluoromethylthiopyrazole, m.p. about 106° C.;
18. 3-Cyano-1-(2,6-dichloro-4-trifluoromethylphenyl)-5-diethoxymethyl-4-trifluoromethylthiopyrazole, m.p. about 72° C.;
19. 3-Cyano-1-(2,6-dichloro-4-trifluoromethylphenyl)-5-diethoxymethyl-4-trifluoromethylsulfonylpyrazole, m.p. about 100° C.;
20. 3-Cyano-1-(2,6-dichloro-4-trifluoromethylphenyl)-5-diethoxymethyl-4-trifluoromethylsulfinylpyrazole, m.p. 132° C.;
21. 3-Cyano-1-(2,6-dichloro-4-trifluoromethylphenyl)-5-(1-acetoxyethenyl)-4-trifluoromethylsulfonylpyrazole, m.p. 121° C.;

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, plant nematodes, or helminth or protozoan pests, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, foliar insecticidal, soil insecticidal and nematicidal, systemic, antifeeding or pesticidal activity via seed treatment.

A fourth object of the present invention is to provide compounds with substantially enhanced and more rapid activity, especially against insects and more particularly insects in their larval stages.

A fifth object of the present invention is to provide compounds with greatly improved (greater and faster) penetration into pest species when topically applied and thus to provide enhanced movement of the compounds to the pesticidal site(s) of action within the pest.

Another object of the present invention is to provide compounds with high activity and improved safety to the user and the environment, which are obtained by optimization of chemical, physical and biological properties such as solubility, melting point, stability, electronic and steric parameters, and the like.

These objects are achieved, in whole or in part, by the present invention.

The compounds of formula (I) can be prepared by the application or adaptation of known methods (i.e., methods heretofore used or described in the chemical literature): generally pyrazole ring formation followed where necessary by changing substituents. It is also to be understood that, in the description of the following processes the sequences for the introduction of the various groups on the pyrazole ring may be performed in a different order and that suitable protecting groups may be required as will be apparent to those skilled in the art.

In the following description of processes when symbols appearing in formulae are not specifically defined, it is to be understood that they are "as defined above" in accordance with the first definition of each symbol in this specification. The term "protection" shall include conversion to a suitable non-reactive group which may be reconverted when desired, as well as the addition of groups which render the functionality non-reactive.

In the description that follows, the ring system:

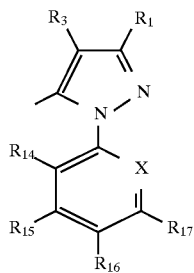

is defined as Q.

According to a feature of the present invention compounds of formula (I) wherein $R_7$ is formyl are formed by oxidative cleavage of the alkene moiety of a compound of formula (II):

 (II)

wherein $R_{25}$ is selected from alkylcarbonyl, alkoxycarbonyl, cyano and nitro. When $R_{25}$ is alkylcarbonyl or alkoxycarbonyl, it is preferably ($C_1$–$C_{12}$ alkyl)carbonyl or ($C_1$–$C_{12}$ alkoxy)carbonyl, most preferably ($C_1$–$C_6$ alkyl)carbonyl or ($C_1$–$C_6$ alkoxy)carbonyl. Such a transformation is well known to those skilled in the art and can be realized with ozone, potassium permanganate, sodium metaperiodate and the like. The process may be carried out optionally in a solvent such as methylene chloride, diethyl ether or chloroform and generally at temperatures between −100° C. and 100° C. A summary of such methods is found in *Comprehensive Organic Transformations*, VCH Publishers, 1989, R. C. Larock, pp. 595–596.

Compounds of formula (II) are novel and constitute a further feature of the invention. Compounds of formula (II) can be prepared by dehydrohalogenation of a compound of formula (III):

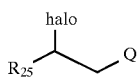 (III)

wherein "halo" represents halogen and $R_{25}$ is defined as above.

This can be effected by reaction of formula (III) compounds with bases such as triethylamine, sodium hydroxide and lithium diisopropylamide. The reaction is carried out optionally in a common organic solvent such as dichloromethane, diethyl ether, tetrahydrofuran, or toluene, and generally between −100° and 100° C. depending on the base used. Compounds of formula (III) are novel and constitute a further feature of the invention.

Compounds of formula (III) can be produced from compounds of formula (IV):

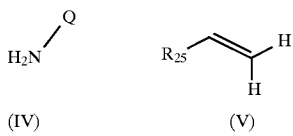

(IV)     (V)

The process is effected by reaction of a compound of formula (IV) with an olefin of formula (V) in the presence of an alkylnitrite and Copper (II) halide, for example, as described in *J. Org. Chem.*, 1977, 42 (14) 2431. Those skilled in the art will recognize this as a Meerwein Arylation. The process is generally carried out in a mixture of the olefin and a common organic solvent, preferably acetonitrile. The process is generally carried out at a temperature from −50° to 100° C., preferably at ambient temperature.

Syntheses of compounds of formula (IV) are described in U.S. Pat. Nos. 5,232,940; 5,306,694; 4,772,312; 4,804,675; and 4,614,533.

According to a further feature of the present invention, compounds of formula (I) above in which $R_7$ is —$CHR_{11}R_{12}$ wherein $R_{11}$ and $R_{12}$ are not cyano and are the same, or in which $R_7$ is

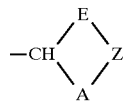

may be prepared by the reaction of the corresponding compound of formula (I) above in which $R_7$ is formyl with a compound of formula (VIa) or (VIb) respectively, wherein $R_{11}$ is not cyano:

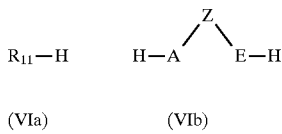

(VIa)     (VIb)

in the presence of a catalyst, such as sulfuric acid, hydrochloric acid, para-toluenesulfonic acid, an acidic resin or a Lewis acid catalyst such as zinc (II) chloride. The process is generally carried out optionally in the presence of a solvent such as dichloromethane or benzene and occurs from −20° C. to 100° C., preferably at the boiling point of the solvent. Those skilled in the art will recognize this reaction as an acetal formation, the general conditions of which are found in *Protective Groups in Organic Synthesis,* 2nd Ed., Wiley-Interscience, 1991, T. W. Greene and P. G. M. Wuts, pp. 175–220. Compounds of formulae (VIa) and (VIb) are known to those skilled in the art as alcohols, amines and thiols.

According to a further feature of the present invention, compounds of formula (I) above in which $R_7$ is —$CHR_{11}$(CN) may be prepared from the corresponding compound of formula (I) in which $R_7$ is —$CHR_{11}R_{12}$ in which $R_{11}$ and $R_{12}$ are the same, by treatment with a trialkylsilylcyanide in the presence of an acid catalyst, preferably a Lewis acid catalyst, e.g. a group IIB, IIA, or IVA halide, such as titanium tetrachloride, in a solvent such as dichloromethane or acetonitrile. Such a process is carried out from −30° to 100° C., preferably from 0° to −20° C. and is described in *Tetrahedron Lett.*, 1984, 25 (31) 3301; *Chem. Lett.*, 1984, 897, and *Bull. Chem. Soc. Jpn.*, 1990, 63, 3122.

According to a further feature of the present invention, compounds of formula (I) above in which $R_7$ is $C_1$–$C_6$ α-hydroxyalkyl or $C_1$–$C_6$ α-hydroxyhaloalkyl may be prepared by the reaction of the corresponding compound of formula (I) in which $R_7$ is formyl with an organometallic reagent or hydride of formula $R_8$—M, wherein M is an alkali or transition metal. The reaction may be performed in a solvent such as a dialkyl ether (e.g. diethyl ether), tetrahydrofuran (THF), or a hydrocarbon (e.g. hexane or toluene) or mixtures thereof. A temperature of from −100° C. to the reflux temperature of the solvent system is generally used.

According to a further feature of the present invention, compounds of formula (I) above in which $R_7$ is $C(O)R_8$ may be prepared by the oxidation of a compound of formula (I) wherein $R_7$ is $C_1$–$C_6$ α-hydroxyalkyl or $C_1$–$C_6$ α-hydroxyhaloalkyl.

This is a reaction well known to those skilled in the art, a summary of which is given in *Comprehensive Organic Transformation*, VCH Publishers, 1989, R. C. Larock, pp. 604–614.

According to a further feature of the present invention, compounds of formula (I) in which $R_7$ is $CR_{13}$=ND may be prepared by the reaction of the corresponding compound of formula (I) in which $R_7$ is $C(O)R_8$ respectively with a compound of formula (VII):

$$D-NH_2 \quad (VII)$$

The process is generally carried out optionally in the presence of a solvent such as ethanol, methylene chloride, or toluene and generally at temperatures between 0° C. and the reflux temperature of the solvent. Those skilled in the art will recognize such reactions as formations of oximes and hydrazones whose methods of synthesis are reviewed in *Advanced Organic Chemistry*, 4th ed., J. Wiley and Sons, 1992, March, pp. 804–806. Compounds of formula (VII) are well known to those skilled in the art or may be prepared by known methods.

According to a further feature of the present invention, compounds of formula (I) above in which $R_7$ is —$C(OR_9)$=$CHR_{10}$ may be prepared by the reaction of the corresponding compound of formula (I) in which $R_7$ is $C(O)R_8$ (and $R_8$ is not H) with a base, followed by treatment with a compound of formula $R_9$-L, wherein L is a leaving group, such as halide anion or sulfonate anion. Suitable bases include triethylamine and lithium diisopropylamide. The process is generally carried out within a range of temperatures, usually between −100° C. and the boiling temperature of the solvent, such as tetrahydrofuran, toluene, diethyl ether and the like. *Modern Organic Chemistry*, 2nd ed., Benjamin Cummings, 1972, H. O. House, p. 763 describes a similar process.

Pesticidally acceptable salts of the compounds of formula (I) may be prepared by known methods.

The following compounds are further examples of the invention. In the table that follows the following abbreviations have been used:

Me=methyl

Et=ethyl

Pr=n-propyl

TABLE I

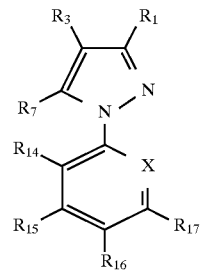

Wherein: $R_1$ = CN; $R_{15}$ = $R_{17}$ = H; $R_{14}$ = Cl; $R_{16}$ = $CF_3$

| $R_3$ | X | $R_7$ |
|---|---|---|
| $SCF_3$ | C—Cl | COEt |
| $SCF_3$ | C—Cl | COPr |
| $SCF_3$ | C—Cl | CH(OEt)CN |
| $SCF_3$ | C—Cl | CH=NOH |
| $SOCF_3$ | C—Cl | COEt |
| $SOCF_3$ | C—Cl | COPr |
| $SOCF_3$ | C—Cl | CH(OEt)CN |
| $SOCF_3$ | C—Cl | CH=NOH |
| $SOCF_3$ | C—Cl | CH=$NNH_2$ |
| $SO_2CF_3$ | C—Cl | COEt |
| $SO_2CF_3$ | C—Cl | COPr |
| $SO_2CF_3$ | C—Cl | CH(OEt)CN |
| $SO_2CF_3$ | C—Cl | CH=NOH |
| $SO_2CF_3$ | C—Cl | CH=$NNH_2$ |
| $SCCl_2F$ | C—Cl | COEt |
| $SCCl_2F$ | C—Cl | COPr |
| $SCCl_2F$ | C—Cl | $CH(OMe)_2$ |
| $SCCl_2F$ | C—Cl | $CH(OEt)_2$ |
| $SCCl_2F$ | C—Cl | CH(OMe)CN |
| $SCCl_2F$ | C—Cl | CH=NOH |
| $SCCl_2F$ | C—Cl | CH=$NNH_2$ |
| $SCCl_2F$ | C—Cl | COMe |
| $SOCCl_2F$ | C—Cl | COMe |
| $SOCCl_2F$ | C—Cl | COEt |
| $SOCCl_2F$ | C—Cl | COPr |
| $SOCCl_2F$ | C—Cl | $CH(OMe)_2$ |
| $SOCCl_2F$ | C—Cl | $CH(OEt)_2$ |
| $SOCCl_2F$ | C—Cl | CH(OMe)CN |
| $SOCCl_2F$ | C—Cl | CH=NOH |
| $SoCCl_2F$ | C—Cl | CH=$NNH_2$ |
| $SO_2CCl_2F$ | C—Cl | COMe |
| $SO_2CCl_2F$ | C—Cl | COEt |
| $SO_2CCl_2F$ | C—Cl | COPr |
| $SO_2CCl_2F$ | C—Cl | CH(OMe) |
| $SO_2CCl_2F$ | C—Cl | CH(OMe)CN |
| $SO_2CCl_2F$ | C—Cl | $CH(oEt)_2$ |
| $SO_2CCl_2F$ | C—Cl | CH=NOH |
| $SO_2CCl_2F$ | C—Cl | CH=$NNH_2$ |
| $SCF_3$ | N | COEt |
| $SCF_3$ | N | COPr |
| $SCF_3$ | N | CH(OEt)CN |
| $SCF_3$ | N | CH=NOH |
| $SOCF_3$ | N | COEt |
| $SOCF_3$ | N | COPr |
| $SOCF_3$ | N | CH(OEt)CN |
| $SOCF_3$ | N | CH=NOH |
| $SOCF_3$ | N | CH=$NNH_2$ |
| $SO_2CF_3$ | N | COEt |
| $SO_2CF_3$ | N | COPr |
| $SO_2CF_3$ | N | CH(OEt)CN |
| $SO_2CF_3$ | N | CH=NOH |
| $SO_2CF_3$ | N | CH=$NNH_2$ |
| $SCCl_2F$ | N | COEt |
| $SCCl_2F$ | N | COPr |
| $SCCl_2F$ | N | $CH(OMe)_2$ |
| $SCCl_2F$ | N | $CH(OEt)_2$ |
| $SCCl_2F$ | N | CH(OMe)CN |

TABlE I-continued

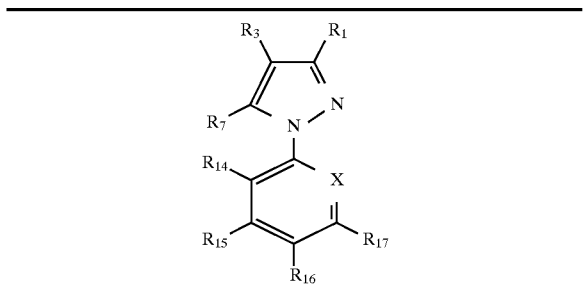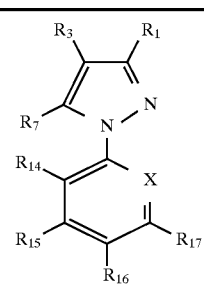

Wherein: $R_1$ = CN; $R_{15}$ = $R_{17}$ = H; $R_{14}$ = Cl; $R_{16}$ = $CF_3$

| $R_3$ | X | $R_7$ |
|---|---|---|
| $SCCl_2F$ | N | CH=NOH |
| $SCCl_2F$ | N | CH=$NNH_2$ |
| $SCCl_2F$ | N | COMe |
| $SOCCl_2F$ | N | COMe |
| $SOCCl_2F$ | N | COEt |
| $SOCCl_2F$ | N | COPr |
| $SOCCl_2F$ | N | $CH(OMe)_2$ |
| $SOCCl_2F$ | N | $CH(OEt)_2$ |
| $SOCCl_2F$ | N | CH(OMe)CN |
| $SOCCl_2F$ | N | CH=NOH |
| $SOCCl_2F$ | N | CH=$NNH_2$ |
| $SO_2CCl_2F$ | N | COMe |
| $SO_2CCl_2F$ | N | COEt |
| $SO_2CCl_2F$ | N | COPr |
| $SO_2CCl_2F$ | N | CH(OMe) |
| $SO_2CCl_2F$ | N | CH(OMe)CN |
| $SO_2CCl_2F$ | N | $CH(OEt)_2$ |
| $SO_2CCl_2F$ | N | CH=NOH |
| $SO_2CCl_2F$ | N | CH=$NNH_2$ |
| $SCF_3$ | C—Cl | COMe |
| $SCF_3$ | C—Cl | COEt |
| $SCF_3$ | C—Cl | COPr |
| $SCF_3$ | C—Cl | CH(OEt)CN |
| $SCF_3$ | C—Cl | CH NOH |
| $SOCF_3$ | C—Cl | COEt |
| $SOCF_3$ | C—Cl | COPr |
| $SOCF_3$ | C—Cl | CH(OEt)CN |
| $SOCF_3$ | C—Cl | CH=NOH |
| $SOCF_3$ | C—Cl | CH=$NNH_2$ |
| $SO_2CF_3$ | C—Cl | COEt |
| $SO_2CF_3$ | C—Cl | COPr |
| $SO_2CF_3$ | C—Cl | CH(OEt)CN |
| $SO_2CF_3$ | C—Cl | CH=NOH |
| $SO_2CF_3$ | C—Cl | CH=$NNH_2$ |
| $SCCl_2F$ | C—Cl | COEt |
| $SCCl_2F$ | C—Cl | COPr |
| $SCCl_2F$ | C—Cl | $CH(OMe)_2$ |
| $SCCl_2F$ | C—Cl | $CH(OEt)_2$ |
| $SCCl_2F$ | C—Cl | CH(OMe)CN |
| $SCCl_2F$ | C—Cl | CH=NOH |
| $SCCl_2F$ | C—Cl | CH=$NNH_2$ |
| $SCCl_2F$ | C—Cl | COMe |
| $SOCCl_2F$ | C—Cl | COMe |
| $SOCCl_2F$ | C—Cl | COEt |
| $SOCCl_2F$ | C—Cl | COPr |
| $SOCCl_2F$ | C—Cl | $CH(OMe)_2$ |
| $SOCCl_2F$ | C—Cl | $CH(OEt)_2$ |
| $SOCCl_2F$ | C—Cl | CH(OMe)CN |
| $SOCCl_2F$ | C—Cl | CH=NOH |
| $SOCCl_2F$ | C—Cl | CH=$NNH_2$ |
| $SO_2CCl_2F$ | C—Cl | COMe |
| $SO_2CCl_2F$ | C—Cl | COEt |
| $SO_2CCl_2F$ | C—Cl | COPr |
| $SO_2CCl_2F$ | C—Cl | CH(OMe) |
| $SO_2CCl_2F$ | C—Cl | CH(OMe)CN |
| $SO_2CCl_2F$ | C—Cl | $CH(OEt)_2$ |
| $SO_2CCl_2F$ | C—Cl | CH=NOH |
| $SO_2CCl_2F$ | C—Cl | CH=$NNH_2$ |
| $SCF_3$ | N | COMe |
| $SCF_3$ | N | COEt |
| $SCF_3$ | N | COPr |
| $SCF_3$ | N | CH(OEt)CN |
| $SCF_3$ | N | CH NOH |
| $SOCF_3$ | N | COMe |
| $SOCF_3$ | N | COEt |
| $SOCF_3$ | N | COPr |
| $SOCF_3$ | N | CH(OEt)CN |
| $SOCF_3$ | N | CHNOH |
| $SOCF_3$ | N | CH=$NNH_2$ |
| $SO_2CF_3$ | N | COMe |
| $SO_2CF_3$ | N | COEt |
| $SO_2CF_3$ | N | COPr |
| $SO_2CF_3$ | N | CH(OEt)CN |
| $SO_2CF_3$ | N | CH=NOH |
| $SO_2CF_3$ | N | CH=$NNH_2$ |
| $SCCl_2F$ | N | COEt |
| $SCCl_2F$ | N | COPr |
| $SCCl_2F$ | N | $CH(OMe)_2$ |
| $SCCl_2F$ | N | $CH(OEt)_2$ |
| $SCCl_2F$ | N | CH(OMe)CN |
| $SCCl_2F$ | N | CH=NOH |
| $SCCl_2F$ | N | CH=$NNH_2$ |
| $SCCl_2F$ | N | COMe |
| $SOCCl_2F$ | N | COMe |
| $SOCCl_2F$ | N | COEt |
| $SOCCl_2F$ | N | COPr |
| $SOCCl_2F$ | N | $CH(OMe)_2$ |
| $SOCCl_2F$ | N | $CH(OEt)_2$ |
| $SOCCl_2F$ | N | CH(OMe)CN |
| $SOCCl_2F$ | N | CH=NOH |
| $SOCCl_2F$ | N | CH=$NNH_2$ |
| $SO_2CCl_2F$ | N | COMe |
| $SO_2CCl_2F$ | N | COEt |
| $SO_2CCl_2F$ | N | COPr |
| $SO_2CCl_2F$ | N | CH(OMe) |
| $SO_2CCl_2F$ | N | CH(OMe)CN |
| $SO_2CCl_2F$ | N | $CH(OEt)_2$ |
| $SO_2CCl_2F$ | N | CH=NOH |
| $SO_2CCl_2F$ | N | CH=$NNH_2$ |

The following non-limiting EXAMPLES 1 to 15 illustrate detailed methods of synthesis and the physical properties of representative pesticidal compounds of formula (I) (and their chemical intermediates) according to the invention. Additionally, one or more spectroscopic analyses (IR, $H^1$ or $F^{19}$ NMR, MS, etc.) have been performed on each compound for characterization and confirmation of the chemical structure.

EXAMPLE 1

Preparation of 5-(2'-bromo-2'-carbomethoxy)ethyl-3-cyano-1-(2,6-dichloro-4-trifluoromethylphenyl)-4-trifluoromethylthiopyrazole.

A solution of 5-amino-3-cyano-1-(2,6-dichloro-4-trifluoromethylphenyl)-4-trifluoromethylthiopyrazole (100 g, 0.24 mol) and acetonitrile was added dropwise to a solution of methyl acrylate (430 ml, 4.78 mol), copper (II) bromide (80 g, 0.036 mol), 90% tert-butylnitrite (51 ml, 0.39 mol) and acetonitrile (400 ml) at 0° C. After warming to room temperature, the reaction was stirred 12 hours. The mixture was diluted with diethyl ether and washed with water. After drying over magnesium sulfate, the organic layer was concentrated under reduced pressure. Trituration from hexanes gave the title compound as a white solid (72.7g) m.p. about 122° C.

EXAMPLE 2

Preparation of 3-cyano-1-(2,6-dichloro-4-trifluoromethylphenyl)-5-(E-2-methoxycarbonylethenyl)-4-trifluoromethylthiopyrazole.

The product of Example 1 (45 g, 0.079 mol) was dissolved in toluene (60 ml) and 1,8-diazabicyclo-[5,4,0]-undec-7-ene (13 ml, 0.087 mol) added. After stirring for 30 minutes, the mixture was diluted with ethyl acetate, washed with water, 10% aqueous hydrochloric acid solution, saturated aqueous sodium hydrogen carbonate solution and saturated sodium chloride solution. The organic phase was dried over magnesium sulfate, filtered and concentrated under reduced pressure. The remaining oil was triturated under cold pentane to leave the title compound as a white solid (36.6 g), m.p. about 90° C.

EXAMPLE 3

Preparation of 3-cyano-1-(2,6-dichloro-4-trifluoromethylphenyl)-5-formyl-4-trifluoromethylthiopyrazole.

Ozone was bubbled through a solution of the product of Example 2 (36.6 g, 0.075 mol) in dichloromethane (1.8 L) at -78° C. After 3 hours the intensely blue solution was decolorized with oxygen gas, then treated with dimethylsulfide (19 ml, 0.26 mol). This was allowed to warm to room temperature over a 14 hour period whereupon the mixture was washed with water, dried over magnesium sulfate, filtered and concentrated under reduced pressure to provide the title compound as white crystals (30.7 g), m.p. about 90° C.

EXAMPLE 4

Preparation of 3-cyano-1-(2,6-dichloro-4-trifluoromethylphenyl)-5-dimethoxymethyl-4-trifluoromethylthiopyrazole.

The product of Example 3 (2.0 g, 0.005 mol) was combined with trimethylorthoformate (10 ml, 0.09 mol) and para-toluenesulfonic acid monohydrate (50 mg, catalytic) in anhydrous methanol. The mixture was refluxed for 72 hours, cooled to room temperature, poured into diethyl ether, washed with a 1:1 mixture of 10% aqueous sodium hydroxide solution and concentrated aqueous sodium chloride solution (100 ml), water (100 ml) and saturated aqueous sodium chloride solution (100 ml). The organic phase was dried over magnesium sulfate, filtered and concentrated in vacuo to leave an oil that was purified by silica gel chromatography using a 3:1 hexane:dichloromethane solvent mixture. This provided the title compound as a white solid (1.83 g), m.p. about 93° C. Also prepared by this method: Compound 18.

EXAMPLE 5

Preparation of 3-cyano-5-(1-cyano-1-methoxy)methyl-1-(2,6-dichloro-4-trifluoromethylphenyl)-4-trifluoromethylthiopyrazole.

The product of Example 4 (3.0 g, 6.3 mmol) was combined with trimethylsilylcyanide (2.5 ml, 18.9 mmol) in acetonitrile and cooled to 0° C. Boron trifluoride ethereate (74 μl, 0.6 mmol) was added, the mixture stirred 5 minutes and warmed to room temperature. After 1.25 hours, the mixture was poured into saturated aqueous sodium hydrogen carbonate solution and washed with diethyl ether. The combined organic phases were washed with water, saturated aqueous sodium chloride solution, dried over magnesium sulfate, filtered and concentrated under reduced pressure. Removal of solvents in vacuo provided the title compound as a yellow oil (2.99 g). 1H-NMR (300 MHz, CDCl$_3$): d 7.69 (m, 2H); 5.28 (s, 1H); 3.35 (s, 3H).

EXAMPLE 6

Preparation of 5-(1-O-acetylethenyl)-3-cyano-1-(2,6-dichloro-4-trifluoromethylphenyl)-4-trifluoromethylsulfonylpyrazole.

A solution of 5-bromo-3-cyano-1-(2,6-dichloro-4-trifluoromethylphenyl)-4-trifluoromethylsulfonylpyrazole (2.3 g, 4.4 mmol, the preparation of which is described in U.S. Pat. No. 5,232,940) in anhydrous tetrahydrofuran, was cooled to -78° C. and treated with n-butyllithium (2.12 ml of 2.5 m solution in hexanes, 5.3 mmol) by dropwise addition. After 2 hours, the mixture was treated with acetyl chloride (0.37 ml, 5.3 mmol) over 10 minutes. After warming to room temperature and stirring 14 hours, the mixture was poured onto ice and washed with diethyl ether. The combined organic phases were washed with water, saturated aqueous sodium chloride solution, dried over magnesium sulfate, filtered and concentrated under reduced pressure. Chromatography of the resulting oil in ethylacetate:hexanes left the title compound as a white solid (0.52 g), m.p. about 121° C.

EXAMPLE 7

Preparation of 5-acetyl-3-cyano-1-(2,6-dichloro-4-trifluoromethylphenyl)-4-trifluoromethylsulfonylpyrazole.

The product of Example 6 (150 mg, 0.3 mmol) was dissolved in tetrahydrofuran and treated with a 6M aqueous hydrochloric acid solution (1 ml, 6 mmol) and the resulting solution heated to reflux for 22 hours. The mixture was cooled to room temperature, washed with diethyl ether and the organic phase dried over magnesium sulfate. After filtering and concentrating under reduced pressure, the residue was chromatographed on silica gel with ethylacetate::hexanes to provide the title compound as a white solid (120 mg), m.p. about 161° C.

EXAMPLE 8

Preparation of 3-cyano-1-(2,6-dichloro-4-trifluoromethylphenyl)-5-(1-hydroxyethyl)-4-trifluoromethylthiopyrazole.

Copper (I) iodide (6.1 g, 0.032 mol) was suspended in anhydrous diethyl ether and cooled to 0° C. Methyllithium (1.6M in diethyl ether, 40 ml, 0.064 mol) was added via cannula and stirred 10 minutes. A solution of the product of Example 3 (10 g, 0.023 mol) in diethyl ether was added via cannula creating a bright yellow suspension. After 15 minutes, 10% aqueous hydrochloric acid (40 ml) was added while venting the reaction vessel. The remaining suspension was filtered through Celite® and washed with diethyl ether several times. The organic phase was washed with saturated sodium hydrogen carbonate solution, saturated aqueous sodium chloride solution, dried over magnesium sulfate, filtered and concentrated under reduced pressure. Trituration from pentane provided crystals that were purified by silica gel chromatography using ethyl acetate:hexanes. The title compound was isolated as a white solid (7.56 g), m.p. about 123° C.

EXAMPLE 9

Preparation of 5-acetyl-3-cyano-1-(2,6-dichloro-4-trifluoromethylphenyl)-4-trifluoromethylthiopyrazole.

The product of Example 8 (2.8 g, 0.0062 mol) was combined with Celite® (3.0 g) in dichloromethane. Pyridinium chlorochromate (1.7 g, 0.0079 mol) was added in one portion and the slurry stirred 6 hours. Another portion of oxidant (0.9 g) was added and the mixture stirred an additional 18 hours. The mixture was diluted with diethyl ether, filtered through Florisil®, and the filtrate concentrated under reduced pressure. The title compound was isolated as a white solid (2.72 g), m.p. about 128° C.

EXAMPLE 10

Preparation of 5-acetyl-3-cyano-1-(2,6-dichloro-4-trifluoromethylphenyl)-4-trifluoromethylsulfinylpyrazole.

The product of Example 8 (0.80 g, 118 mmol) was dissolved in trifluoroacetic acid (8 ml), cooled to 0° C. and treated with a 30% aqueous solution of hydrogen peroxide (0.18 ml, 1.8 mmol). After 14 hours at 0° C., more hydrogen peroxide solution was added (0.25 ml, 2.5 mmol) and the mixture stirred 14 hours at 0° C. The mixture was then poured into water which precipitated a white solid. This solid was filtered, washed with water, dissolved in dichloromethane, dried over sodium sulfate, filtered and concentrated under reduced pressure. The residue was purified by silica gel chromatography using an ethyl acetate:hexanes solvent gradient. The title compound was isolated as a white solid (0.4 g), m.p. about 156° C. Also prepared by this method: Compounds 12, 14, and 16.

EXAMPLE 11

Preparation of 5-[(N-amino)iminomethylidenyl]-3-cyano-1-(2,6-dichloro-4-trifluoromethylphenyl)-5-trifluoromethylthiopyrazole.

The product of Example 3 (2.0 g, 4.6 mmol) was combined with hydrazine (0.25 ml, 7.8 mmol) in anhydrous ethanol and heated to reflux until analytical thin layer chromatography indicated the reaction was complete. The mixture was cooled to room temperature, concentrated under reduced pressure, and diluted with ethyl acetate. The organic phase was washed with water, concentrated aqueous sodium chloride solution, dried over magnesium sulfate, filtered and concentrated under reduced pressure. Silica gel chromatography using an ethyl acetate:hexanes gradient provided the title compound as a white solid (0.44 g) m.p. about 130° C. Also prepared by this method: Compound 11.

EXAMPLE 12

Preparation of 3-cyano-1-(2,6-dichloro-4-trifluoromethylphenyl)-5-[(N-methoxy)iminomethylidenyl]-4-trifluoromethylthiopyrazole.

The product of Example 3 (1.0 g, 2.3 mmol) was combined with methoxyamine hydrochloride (192 mg, 2.3 mmol) and sodium acetate trihydrate (314 mg, 2.3 mmol) in anhydrous ethanol and heated to reflux for 20 hours. The mixture was cooled to room temperature, concentrated under reduced pressure and diluted with diethyl ether. The organic phase was washed with water, saturated aqueous sodium chloride solution, dried over magnesium sulfate, filtered and concentrated under reduced pressure. The residue was purified by silica gel chromatography using ethyl acetate:hexanes. The title compound was isolated as a 3:1 mixture of isomers (317 mg), m.p. about 87° C.

EXAMPLE 13

Preparation of 3-cyano-1-(2,6-dichloro-4-trifluoromethylphenyl)-5-hydroxymethyl-4-trifluoromethylthiopyrazole.

The product of Example 3 (5.0 g, 0.012 mol) was added to a mixture of sodium borohydride (0.5 g, 0.013 mol) in anhydrous ethanol at 5° C. After 1 hour, 10% aqueous hydrochloric acid solution (35 ml) was added slowly with copious gas evolution. The mixture was poured into water and washed with diethyl ether. The organic phase was washed with saturated sodium chloride solution, dried over magnesium sulfate, filtered and concentrated under reduced pressure to provide the title compound as a white solid, m.p. 118° C.

EXAMPLE 14

Preparation of 3-cyano-1-(2,6-dichloro-4-trifluoromethylphenyl)-5-dimethoxy-4-trifluoromethylsulfinylpyrazole.

The product of Example 4 (1.83 g, 0.0038 mol) was combined with meta-chloroperbenzoic acid (80% weight, 0.9 g, 0.0042 mol) in dichloromethane at 0° C. After 6 hours, the mixture was warmed to room temperature and stirred 11 hours. This was heated to reflux for 7 hours whereupon more metα-chloroperbenzoic acid (80% weight, 0.9 g, 0.0042 mol) was added and the reaction heated an additional 47 hours. The mixture was cooled to room temperature, poured into saturated aqueous sodium bicarbonate solution and washed with diethyl ether. The combined organic extracts were washed with saturated aqueous sodium bisulfite solution and saturated aqueous sodium chloride solution. The organic layer was dried over sodium sulfate, filtered and solvents removed under reduced pressure to leave an oil that was purified by silica gel chromatography using a hexanes:ethyl acetate mixture. The product (0.74 g) was isolated as a solid, m.p. about 116° C. Also prepared by this method: Compounds 15, 19, and 20.

EXAMPLE 15

Preparation of 3-cyano-1-(2,6-dichloro-4-trifluoromethylphenyl)-5-(1-hydroxy-2,2,2-trifluoroethyl)-4-trifluoromethylthiopyrazole.

The product of Example 3 (2.0 g, 0.0046 mol) was dissolved in anhydrous tetrahydrofuran (10 mL). Trifluoromethyltrimethylsilane (0.8 mL, 0.0055 mol) was added and the reaction cooled to 0° C. Tetrabutylammoniumfluoride (TBAF, 50 µL, cat.) was added. After intervals of 20 minutes, 1.5 hours, and 18 hours, aliquots of TBAF (50 µL) were added at 0° C. followed by warming to room temperature. After 21 hours, more trifluoromethyltrimethylsilane (0.8 mL, 0.0055 mol) was added and the reaction stirred for 5 days. This was poured into 10% hydrochloric acid (100 mL) and washed with diethyl ether (3×50 mL). The combined organic extracts were washed with saturated aqueous sodium chloride solution, dried over magnesium sulfate, filtered and evaporated to an oil. This was purified by silica gel chromatography using an ethyl acetate in hexanes gradient to provide the title compound (1.08 g) as a white solid, m.p. about 106° C.

The following representative test procedures, using compounds of the invention, were conducted to determine the pesticidal use and activity of compounds of the invention against: a tick; certain insects, including aphids, caterpillars, a fly, a beetle larvae, a cockroach, a flea, two species of corn rootworm, a cutworm; and a nematode. The specific species tested were as follows:

| GENUS, SPECIES | COMMON NAME | ABBREVIATION |
|---|---|---|
| *Aphis nasturtii* | buckthorn aphid | BA |
| *Aphis gossypii* | cotton aphid | CA |
| *Schizaphis graminum* | greenbug aphid | GA |
| *Spodoptera eridania* | southern armyworm | SAW |
| *Heliothis virescens* | tobacco budworm | TBW |
| *Musca domestica* | house fly | HF |
| *Epilachna varivestis* | Mexican bean beetle | MBB |
| *Periplaneta americana* | American cockroach | ACR |
| *Rhipicephalus sanguineus* | dog tick | DT |
| *Ctenocephalides felis* | cat flea | CF |
| *Meloidogyne incognita* | southern root-knot nematode | SRKN |
| *Diabrotica virgifera virgifera* | western corn rootworm | WCRW |
| *Diabrotica undecimpunctata howardi* | southern corn rootworm | SCRW |
| *Agrotis ipsilon* | black cutworm | BCW |

The test compounds were formulated for use according to the following methods.

For the tick, aphids, southern armyworm, tobacco budworm, house fly, Mexican bean beetle, American cockroach, cat flea, southern corn rootworm, western corn rootworm, black cutworm, and southern root-knot nematode, a solution or suspension was prepared by adding the test compound to a solution of dimethylformamide, acetone, emulsifiers which are alkylaryl polyether alcohols organic sulfonates, and water. The result was a 100 or 500 ppm concentration of the test compound.

For house fly tests, the water-acetone-DMF-emulsifier solution was adjusted with a 20% by weight aqueous solution of sucrose to provide a final 100 or 250 ppm concentration of the test compound.

For the western corn rootworm test, the water-acetone-DMF-emulsifier solution was adjusted for a treatment rate of 0.15 or 0.5 ppm.

For southern corn rootworm and black cutworm tests, the water-acetone-DMF-emulsifier solution was adjusted for a treatment rate of 2.5, 5, 6.75 or 10 ppm.

For cotton aphid systemic tests and black cutworm—systemic tests, the water-acetone-DMF-emulsifier solution was adjusted for a treatment rate of 10.0 ppm soil concentration.

For the greenbug aphid systemic test, the water-acetone-DMF-emulsifier solution was adjusted for a treatment rate of 10 or 25 ppm soil concentration.

For the southern root-knot nematode tests, the water-acetone-DMF-emulsifier solution was adjusted for a treatment rate of 23 kg/ha soil concentration.

The above formulated test compounds were evaluated for their pesticidal activity at specified concentrations, in ppm (parts per million) by weight or in kg/ha (kilograms per hectare). The following procedures were used to evaluate a number of compounds within the scope of the invention.

Buckthorn aphid (BA) or cotton aphid (CA): Adult and nymphal stages of buckthorn or cotton aphid were reared on potted dwarf nasturtium or cotton plants, respectively. Plants infested with 100–150 aphids were wet to runoff with the 100 or 500 ppm test compound formulation. As an untreated control, a water-acetone-DMF-emulsifier solution containing no test compound was also applied to runoff to infested plants. The treated plants were stored for one day for buckthorn aphid and three days for cotton aphid, after which the dead aphids were counted.

Southern armyworm (SAW), Mexican bean beetle (MBB): Bean leaves were wet to runoff with the 100 or 500 ppm test compound formulation. As an untreated control, a water-acetone-DMF-emulsifier solution containing no test compound was also applied wet to runoff to bean leaves. Five or six randomly selected second instar southern armyworm larvae or Mexican bean beetle larvae were introduced into each plastic container with the dry treated leaves. The container was closed and held for five days. Larvae which were unable to move the length of the body, even upon stimulation by prodding, were considered dead.

Tobacco budworm (TBW): Cotton leaves were wet to runoff with the 100 ppm test compound formulation. As an untreated control, a water-acetone-DMF-emulsifier solution containing no test compound was also applied wet to runoff to cotton leaves. Ten randomly selected second instar tobacco budworm larvae were introduced into plastic containers in which moist dental wicks and the dry treated leaves had been placed. The cups were closed and held for five days. Larvae which were unable to move the length of the body, even upon stimulation by prodding, were considered dead.

House fly (HF): Four to six day old adult house flies were used. The flies were immobilized by anesthetizing with carbon dioxide. A bait cup was prepared which contained the 100 or 250 ppm test compound formulation/sucrose solution and one or two absorbent cotton pad(s). As an untreated control, a water-acetone-DMF-emulsifier-sucrose solution containing no test compound was applied in a similar manner. The bait cup was introduced inside the cage prior to admitting 12–25 anesthetized flies. Mortality was assessed after 24 hours.

American cockroach (ACR): Cat food or dog food pellets were added to jars containing 1–2 mls of the 500 ppm test formulation. As an untreated control, an aliquot of a water-acetone-DMF-emulsifier solution containing no test compound was applied in a similar manner. After 48 hours, roach nymphs were added to the jar. Contact and feeding mortality was assessed 1 and 5 days after infestation.

Cat flea (CF), dog tick (DT): Filter papers were treated with an aliquot of the 500 ppm test formulation. As an untreated control, an aliquot of a water-acetone-DMF-emulsifier solution containing no test compound was applied in a similar manner. When dry, 2 treated filters were placed in a vial for the flea and another 2 filters in a vial for the tick. Five adult fleas were added to one vial and 5 adult ticks to the second vial. Contact mortality was assessed 1 day after infestation for the flea and 14 days after infestation for the tick.

Southern root-knot nematode (SRKN): Eggs and second stage juveniles (J2s) of southern root-knot nematodes were obtained from infected roots of reared tomato plants. Pots containing moist soil were treated with the test compound solution for a treatment rate of 23 kg/ha. As an untreated control, an aliquot of a water-acetone-DMF-emulsifier solution containing no test compound was applied in a similar manner. Immediately after treatment, eggs or J2s of southern root-knot nematode were added to the treated soil. For tests with cotton, the seeds were placed on top of the soil the day of treatment and inoculation. For the tests with tomato, the seedlings were transplanted in the pot three days after treatment. The pots were kept in the greenhouse for 2–3 weeks. At the termination of the test, roots of the tomato or cotton seedling were evaluated for galling on a rating scale from 1 to 5 with one equal to severe galling, relative to untreated control, and five to no galling, i.e., complete control.

Western corn rootworm (WCRW): The 500 ppm test formulation was applied to dry sandy loam soil contained in a glass jar for a soil concentration of 0.15 or 0.5 ppm. As an untreated control, an aliquot of a water-acetone-DMF-emulsifier solution containing no test compound was applied in a similar manner. After incubating covered for 24 hours, the soil was mixed and four germinated corn seedlings were added to the jar. Ten neonate western corn rootworm larvae were placed in the jar. Six days after infestation, mortality was assessed by Berlese funnel extraction.

Southern corn rootworm (SCRW), Black cutworm (BCW): Corn seeds were placed in a glass jar and covered with dry sandy loam soil. The 500 ppm test formulation was applied for a soil concentration of 2.5, 5, 6.75 or 10 ppm. As an untreated control, an aliquot of a water-acetone-DMF-emulsifier solution containing no test compound was applied in a similar manner. After incubating covered for 24 hours, the soil was mixed and inoculated with approximately 25 southern corn rootworm eggs. Following an additional 48 hours, two late second to early third instar black cutworms were placed in the jar with a portion of insect diet. Eight days after infestation, mortality was assessed visually for cutworm and by Berlese funnel extraction for rootworm.

Black cutworm—systemic test (BCW-Sys): Corn seeds were placed on top of the soil surface in pots containing moist soil. The test compound solution was applied as a drench to the top of the soil and seeds for a treatment rate equivalent to 10.0 ppm soil concentration. As an untreated control, an aliquot of a water-acetone-DMF-emulsifier solution containing no test compound was applied in a similar manner. The soil surface and seeds were covered with moist soil. The pots were held in the greenhouse for the duration of the bioassay. Ten days after treatment, the corn seedling was clipped and placed in a plastic cup with 2 late second to early third instar black cutworm larvae. Mortality was assessed visually 4 days after infestation.

Greenbug aphid—systemic test (GA-Sys): Sorghum seeds were placed on top of the soil surface in pots containing moist soil. The test compound solution was applied as a drench to the top of the soil and seeds for a treatment rate equivalent to 10 or 25 ppm soil concentration. As an untreated control, an aliquot of a water-acetone-DMF-emulsifier solution containing no test compound was applied in a similar manner. The soil surface and seeds were covered with moist soil. The pots were held in the greenhouse for the duration of the bioassay. When the sorghum seeds germinated, greenbug aphids were sprinkled evenly over the sorghum pots to about 50 aphids per pot. The plants were rated for aphid control one and three days after infestation.

Cotton aphid-systemic test (CA—Sys): Cotton seeds were placed on top of the soil surface in pots containing moist soil. The test compound solution was applied as a drench to the top of the soil and seeds for a treatment rate equivalent to 10.0 ppm soil concentration. As an untreated control, an aliquot of a water-acetone-DMF-emulsifier solution containing no test compound was applied in a similar manner. The soil surface and seeds were covered with moist soil. The pots were held in the greenhouse for the duration of the bioassay. When the cotyledons of the cotton were expanded (approximately 7 days after planting), the cotton was infested with approximately 25 cotton aphids (mixed population). The plants were rated for aphid control three and six days after infestation.

The above procedures were used to evaluate a number of compounds within the scope of the invention. The following compounds in Table II were active against 1 or more insects described above up to 100% mortality. This activity is indicated by a "+."

TABLE II

| CPD no. | BA | CA | SAW | TBW | HF | MBB | ACR | DT | CF | SRKN | WCRW | SCRW | BCW | BCW-Sys | GA-Sys | CA-Sys |
|---|---|---|---|---|---|---|---|---|---|---|---|---|---|---|---|---|
| 1 | + |   | + | + | + | + |   |   |   |   |   | + |   |   |   |   |
| 2 |   |   | + |   | + |   |   |   |   |   | + | + |   |   |   |   |
| 3 |   |   |   | + | + |   |   |   |   |   |   | + | + |   |   |   |
| 4 |   | + |   |   | + |   |   |   |   |   | + | + |   |   |   |   |
| 5 | + |   |   |   | + |   |   |   |   |   | + | + |   |   |   | + |
| 6 | + | + |   |   | + |   |   |   |   |   | + | + |   |   |   |   |
| 7 |   | + |   |   |   |   |   |   |   |   |   |   |   |   |   |   |
| 8 |   |   |   |   |   |   |   |   |   |   |   |   | + | + |   |   |
| 9 |   | + |   |   |   |   |   |   |   |   |   |   |   |   |   |   |
| 10 |   | + |   | + |   | + |   |   |   |   | + | + | + | + | + |   |
| 11 |   |   |   |   | + |   |   |   |   |   | + | + |   |   |   |   |
| 12 |   | + |   |   | + |   |   |   | + |   |   | + |   | + | + |   |
| 13 | + | + | + | + |   | + |   | + |   | + | + |   |   |   |   |   |
| 14 | + | + | + | + |   | + |   | + |   |   | + | + |   |   |   |   |
| 15 | + | + |   | + |   | + |   | + |   |   | + | + |   |   |   |   |
| 16 |   | + | + | + |   | + |   |   |   |   | + | + |   |   |   |   |
| 17 |   |   | + |   | + |   |   |   |   |   | + | + |   |   |   | + |
| 18 |   | + |   | + |   | + | + | + |   |   | + | + |   |   |   |   |
| 19 |   | + | + | + |   | + |   | + |   |   | + |   |   |   |   |   |
| 20 | + | + |   | + |   | + |   | + |   |   |   |   |   |   |   | + |
| 21 | + | + | + | + | + |   |   |   |   |   | + |   |   |   | + |   |

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds of formula (I) or pesticidally acceptable salts thereof thus are advantageously employed in practical uses, for example, in agricultural or horticultural crops, forestry, veterinary medicine or livestock husbandry, or in public health. From this point forward, whenever the term "compounds of formula (I)" is used this term embraces compounds of formula (I) and their pesticidally acceptable salts. The term "compound of formula (I)" embraces a compound of formula (I) and a pesticidally acceptable salt thereof.

The present invention therefore provides a method of control of pests at a locus which comprises the treatment of the locus (e.g., by application or administration) with an effective amount of a compound of formula (I) or a pesticidally acceptable salt thereof, wherein the substituent groups are as hereinbefore defined. The locus includes, for example, the pest itself or the place (plant, animal, person, field, structure, premises, forest, orchard, waterway, soil, plant or animal product, or the like) where the pest resides or feeds.

The compounds of this invention are preferably used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

Furthermore, these compounds may be useful in the control via foliar application or systemic action of some arthropods, especially some insects or mites, which feed on the above ground portions of plants. Control of foliar pests may additionally be provided by application to the plant roots or plant seeds with subsequent systemic translocation to the above ground portions of the plants.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, against attack by arthropods, more especially beetles, including weevils, moths or mites, for example *Ephestia spp.* (flour moths), *Anthrenus spp.* (carpet beetles), *Tribolium spp.* (flour beetles), *Sitophilus spp.* (grain weevils) or *Acarus spp.* (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, *Reticulitermes spp., Heterotermes spp., Coptotermes spp.*

In agriculture against adults, larvae and eggs of Lepidoptera (butterflies and moths), e.g. *Heliothis spp.* such as *Heliothis virescens* (tobacco budworm), *Heliothis armigera* and *Heliothis zea, Spodoptera spp.* such as *S. exempta, S. frugiperda, S. exiqua, S. littoralis* (Egyptian cotton worm), *S. eridania* (southern army worm), and *Mamestra configurata* (bertha army worm); *Earias spp.* e.g. *E. insulana* (Egyptian bollworm), *Pectinophora spp.* e.g. *Pectinophora gossypiella* (pink bollwormn), *Ostrinia spp.* such as *O. nubilalis* (European cornborer), *Trichoplusia ni* (cabbage looper), *Artogeia spp.* (cabbage worms), *Laphygma spp.* (army worms), *Agrotis* and *Amathes spp.* (cutworms), *Wiseana spp.* (porina moth), *Chilo spp.* (rice stem borer), *Tryporyza spp.* and *Diatraea spp.* (sugar cane borers and rice borers), *Sparganothis pilleriana* (grape berry moth), *Cydia pomonella* (codling moth), *Archips spp.* (fruit tree tortrix moth), *Plutella xylostella* (diamond back moth), *Bupalus piniarius, Cheimatobia brumata, Lithocolletis blancardella, Hyponomeuta padella, Plutella maculipennis, Malacosoma neustria, Euproctis chrysorrhoea, Lymantria spp. Bucculatrix thurberiella, Phyllocnistis citrella, Euxoa spp., Feltia brassicae, Panolis flammea, Prodenia litura, Carpocapsa pomonella, Pyrausta nubilalis, Ephestia kuehniella, Galleria mellonella, Tineola bisselliella, Tinea pellionella, Hofmannophila pseudospretella, Cacoecia podana Capus reticulana, Choristoneura fumiferana, Clysia ambiguellis, Homona magnanime* and *Tortix viridana.*

Against adults and larvae of Coleoptera (beetles) e.g. *Hypothenemus hampei* (coffee berry borer), *Hylesinus spp.* (bark beetles), *Anthonomus spp.* e.g. *grandis* (cotton boll weevil), *Acalymma spp.* (cucumber beetles), *Lema spp., Psylliodes spp., Leptinotarsa decemlineata* (Colorado potato beetle), *Diabrotica spp.* (corn rootworms), *Gonocephalum spp.* (false wire worms), *Agriotes spp., Limonius spp.* (wireworms), *Dermolepida spp., Popillia spp., Heteronychus spp.* (white grubs), *Phaedon cochleariae* (mustard beetle), *Epitrix spp.* (flea beetles), *Lissorhoptrus oryzophilus* (rice water weevil), *Meligethes spp.* (pollen beetles), *Ceutorhynchus spp., Rhynchophorus* and *Cosmopolites spp.* (root weevils), *Anobium punctatum, Rhizopertha dominica, Bruchidius obtectus, Acanthoscelides obtectus, Hylotrupes bajulus, Agelastica alni, Psylliodes chrysocephala, Epilachna varivestis, Atomaria spp., Oryzaephilus surinamensis, Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Maligethes aeneus, Ptinus spp., Niptus hololeucrus, Gibbium psylloides, Tribolium spp., Tenebrio molitor, Conoderus spp., Melolontha melolontha, Amphimallon solstitialis* and *Costelytra zealandica.*

Against Heteroptera (Hemiptera and Homoptera) e.g. *Psylla spp., Bemisia spp., Trialeurodes spp., Aphis spp., Myzus spp., Megoura viciae, Phylloxera spp., Adelges spp., Phorodon humuli* (hop damson aphid), *Aeneolamia spp., Nephotettix spp.* (rice leaf hoppers), *Empoasca spp., Nilaparvata spp., Perkinsiella spp., Pyrilla spp., Aonidiella spp.* (red scales), *Coccus spp., Pseucoccus spp., Helopeltis spp.* (mosquito bugs), *Lygus spp., Dysdercus spp., Oxycarenus spp., Nezara spp., Eurygaster spp., Piesma quadrata, Cimex lectularius, Rhodnius prolixus* and *Triatoma spp. Aspidiotus hederae, Aeurodes brassicae, Brevicoryne brassicae, Cryptomyzus ribis, Doralis fabae, Doralis pomi., Eriosoma lanigerum, Hyalopterus arundinis, Macrosiphum avenae, Phorodon humuli, Rhopalosiphum padi, Euscelis bilobatus, Nephotettix cincticeps, Lecanium corni, Saissetia oleae, Laodelphax striatellus.*

Against Hymenoptera e.g. *Athalia spp.* and *Cephus spp.* (saw flies), *Atta spp.* (leaf cutting ants), *Diprion spp.*,

*Hopolocampa spp., Lasius spp., Monomorium spp., Polistes spp., Vespa spp., Vespula spp.,* and *Solenopsis spp.*

Against Diptera e.g. *Delia spp.* (root maggots), *Atherigona spp.* and *Chlorops spp., Sarcophaga spp., Musca spp., Phormia spp., Aedes spp., Anopheles spp., Simulium spp.,* (shoot flies), *Phytomyza spp.* (leaf miners), *Ceratitis spp.* (fruit flies), *Culex spp., Drosophila melanogaster, Ceratitis capitata, Dacus oleae, Tipula paludosa, Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Fannia spp., Bibio hortulanus, Oscinella frit, Phorbia spp., Pegomyia hyoscyani.*

Against Thysanoptera such as *Thrips tabaci, Hercinothrips femoralis,* and *Frankliniella spp.*

Against Orthoptera such as *Locusta* and *Schistocerca spp.* (locusts and crickets), e.g. *Gryllus spp.,* and *Acheta spp.* for example, *Blatta orientalis, Periplaneta americana, Leucophaea maderae, Blatella germanica, Acheta domesticus, Gryllotalpa spp., Locusta migratoria migratorioides, Melanoplus differentialis* and *Schistocerca gregaria.*

Against Collembola e.g. *Sminthurus spp.* and *Onychiurus spp.* (springtails); *Periplaneta spp.* and *Blattela spp.* (roaches).

Against Isoptera e.g. *Odontotermes spp., Reticuletermes spp., Coptotermes spp.* (termites).

Against Dermaptera e.g. *Forticula sp.* (earwigs).

Against arthropods of agricultural significance such as Acari (mites) e.g. *Tetranychus spp., Panonychus spp., Bryobia spp.* (spider mites), *Ornithonyssus spp.* (fowl mites), *Eriophyes spp.* (gall mites), and *Polyphadotarsonemus spp.*

Against Thysanura, for example *Lepisma saccharia.*

Against Anoplura for example, *Phylloxera vastatrix, Pemphigus spp., Pediculus humanus corporis, Haematopinus spp.* and *Linognathus spp.*

Against Mallophaga, for example, *Trichodectes spp.* and *Damalinea spp.*

Against Siphonoptera, for example, *Xenopsylla cheopis* and *Ceratophyllus spp.*

Against other arthopods, such as *Blaniulus spp.* (millipedes), *Scutigerella spp.* (symphilids), *Oniscus spp.* (woodlice) and *Triops spp.* (crustacea).

Against Isopoda, for example, *Oniseus asellus, Armadillidium vulgare* and *Porcellio scaber.*

Against Chilopoda, for example, *Geophilus carpophagus* and *Scutigera spex.*

Against nematodes which attack plants or trees of importance to agriculture, forestry or horticulture either directly or by spreading bacterial, viral, mycoplasma or fungal diseases of the plants, for example, root-knot nematodes such as *Meloidogyne spp.* (e.g. *M. incognita*); cyst nematodes such as *Globodera spp.* (e.g. *G. rostochiensis*); *Heterodera spp.* (e.g. *H. avenae*); *Radopholus spp.* (e.g. *R. similis*); lesion nematodes such as *Pratylenchus spp.* (e.g. *P. pratensis*); *Belonolaimus spp.* (e.g. *B. gracilis*); *Tylenchulus spp.* (e.g. *T. semipenetrans*); *Rotylenchulus spp.* (e.g. *R. reniformis*); *Rotylenchus spp.* (*R. robustus*); *Helicotylenchus spp.* (e.g. *H. multicinctus*); *Hemicycliophora spp.* (e.g. *H. gracilis*); *Criconemoides spp.* (e.g. *C. similis*); *Trichodorus spp.* (e.g. *T. primitivus*); dagger nematodes such as *Xiphinema spp.* (e.g. *X. diversicaudatum*), *Longidorus spp.* (e.g. *L. elongatus*); *Hoplolaimus spp.* (e.g. *H. coronatus*); *Aphelenchoides spp.* (e.g. *A. ritzema-bosi, A. besseyi*); stem and bulb eelworm such as *Ditylenchus spp.* (e.g. *D. dipsaci*).

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. *Ixodes spp., Boophilus spp.* e.g. *Boophilus microplus, Amblyomma spp., Hyalomma spp., Rhipicephalus spp.,* e.g. *Rhipicephalus appendiculatus, Haemaphysalis spp., Dermacentor spp., Ornithodorus spp.* (e.g. *Ornithodorus moubata*)) and mites (e.g. *Damalinia spp., Dermahyssus gallinae, Sarcoptes spp.,* e.g. *Sarcoptes scabiei, Psoroptes spp., Chorioptes spp., Demodex spp., Eutrombicula spp.*); Diptera (e.g. *Aedes spp., Anopheles spp., Musca spp., Hypoderma spp., Gasterophilus spp., Simulium spp*); Hemiptera (e.g. *Triatoma spp*); Phthirapter (e.g. *Damalinia spp., Linognathus spp.*); Siphonaptera (e.g. *Ctenocephalides spp.*); Dictyoptera (e.g. *Periplaneta spp., Blatella spp.*); Hymenoptera (e.g. *Monomorium pharaonis*); for example against infections of the gastro-intestinal tract caused by parasitic nematode worms, for example members of the family Trichostrongylidae, *Nippostrongylus brasiliensis, Trichinella spiralis, Haemonchus contortus, Trichostrongylus colubriformis, Nematodirus batus, Ostertagis circumcincta, Trichostrongylus axei, Cooperia spp.* and *Hymenolepis nana;* in the control and treatment of protozoal diseases caused by, for example, *Eimeria spp.* e.g. *Eimeria tenella, Eimeria acervulina, Eimeria brunetti, Eimeria maxima* and *Eimeria necatrix, Trypanosoms cruzi, Leishaminia spp., Plasmodium spp., Babesis spp., Trichomonadidae spp., Histomanas spp., Giardia spp., Toxoplasma spp., Entamoeba histolytica* and *Theileria spp.*

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 0.01 kg/ha to about 2 kg/ha.

When a pest is soil-borne, the active compound, generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also comprise application to or treatment of the foliage of plants to control arthropods, especially insects or mites, or nematodes attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, or lucerne), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

The compositions hereinafter described for application to growing crops or crop growing loci or as a seed dressing may, in general, alternatively be employed for topical application to man or animals or in the protection of stored products, household goods, property or areas of the general environment. Suitable means of applying the compounds of the invention include:

- to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

- to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

- to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

- to domestic animals in feed to control fly larvae feeding in their feces.

In practice, the compounds of the invention most frequently form parts of compositions. These compositions can be employed to control: arthopods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of formula (I) or a pesticidally acceptable salt thereof, such as described earlier, as the active ingredient in combination or association with one or more other compatible components which are for example, solid or liquid carriers or diluents, adjuvants, surface-active agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions suitable for applications in agriculture, horticulture, or the like include formulations suitable for use as, for example, sprays, dusts, granules, fogs, foams, emulsions, or the like.

Compositions suitable for administration to vertebrates or man include preparations suitable for oral, parenteral, percutaneous, e.g. pour-on, or topical administration.

Compositions for oral administration comprise one or more of the compounds of formula (I), or pesticidally acceptable salts thereof in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastrointestinal tract. Any of these may incorporate the active ingredient contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle, or solid or semisolid subcutaneous implants or pellets designed to release the active ingredient over a protracted period of time and may be prepared and made sterile in any appropriate manner known to the art.

Compositions for percutaneous and topical administration include sprays, dusts, baths, dips, showers, jets, greases, shampoos, creams, wax-smears, or pour-on preparations or devices (e.g. ear tags attached externally to animals in such a way as to provide local or systemic arthropod control).

Solid or liquid baits, suitable for controlling arthropods, comprise one or more compounds of formula (I), or pesticidally acceptable salts thereof, and a carrier or diluent which may include a food substance or some other substance to induce consumption by the arthropod.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethylketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols (particularly alkylphenols or arylphenols), salts of sulfosuccinic acid esters, taurine derivatives (particularly alkyltaurates), phosphoric esters of alcohols or of polycondensates of ethylene oxide with phenols, esters of fatty acids with polyols, or sulfate, sulfonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of formula (I), or pesticidally acceptable salts thereof, which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavoring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimiphos-methyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula (I), or pesticidally acceptable salts thereof, are therefore generally in the form of compositions, which are in various solid or liquid forms.

Solid forms of compositions which can be used are dusting powders (with a content of the compound of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogeneous or heterogeneous compositions containing one or more compounds of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications, be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powders (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The application dose (effective dose) of active ingredient, also as a formulated composition, is generally between about 0.005 and about 15 kg/ha, preferably between about 0.01 and about 2 kg/ha. Therefore, the rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of formula (I) or pesticidally acceptable salts thereof. For administration to animals orally or parenterally, including percutaneously solid or liquid compositions, these normally contain from about 0.1% to about 90% by weight of one or more compounds of formula (I) or pesticidally acceptable salts thereof. Medicated feedstuffs normally contain from about 0.001% to about 3% by weight of one or more compounds of formula (I) or pesticidally acceptable salts thereof. Concentrates or supplements for mixing with feedstuffs normally contain from about 5% to about 90%, preferably from about 5% to about 50%, by weight of one or more compounds of formula (I) or pesticidally acceptable salts thereof. Mineral salt licks normally contain from about 0.1% to about 10% by weight of one or more compounds of formula (I) or pesticidally acceptable salts thereof.

Dusts or liquid compositions for application to livestock, persons, goods, premises or outdoor areas may contain from about 0.0001% to about 15%, more especially from about 0.005% to about 2.0%, by weight, of one or more compounds of formula (I) or pesticidally acceptable salts thereof. Suitable concentrations in treated waters are between about 0.0001 ppm and about 20 ppm, more particularly about 0.001 ppm to about 5.0 ppm of one or more compounds of formula (I), or pesticidally acceptable salts thereof, and may be used therapeutically in fish farming with appropriate exposure times. Edible baits may contain from about 0.01% to about 5%, preferably from about 0.01% to about 1.0%, by weight, of one or more compounds of formula (I) or pesticidally acceptable salts thereof.

When administered to vertebrates parenterally, orally or by percutaneous or other means, the dosage of compounds of formula (I), or pesticidally acceptable salts thereof, will depend upon the species, age, and health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 16-A–16-L illustrate compositions for use against arthropods, especially mites or insects, plant nematodes, or helminth or protozoan pests which comprise, as active ingredient, compounds of formula (I), or pesticidally acceptable salts thereof, such as those described in the preparative examples. The compositions described in EXAMPLES 16-A–16-L can each be diluted to give a sprayable composition at concentrations suitable for use in the field. Generic chemical descriptions of the ingredients (for which all of the following percentages are in weight percent), used in the composition EXAMPLES 16-A–16-L exemplified below, are as follows:

| Trade Name | Chemical Description |
| --- | --- |
| Ethylan BCP | Nonylphenol ethylene oxide condensate |
| Soprophor BSU | Tristyrylphenol ethylene oxide condensate |
| Arytan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No 2 | Sodium lignosulfonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 16-A

A water soluble concentrate is prepared with the composition as follows:

| | |
| --- | --- |
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 16-B

An emulsifiable concentrate (EC) is prepared with the composition as follows:

| | |
| --- | --- |
| Active ingredient | 7% |
| Soprophor BSU | 4% |
| Arylan CA | 4% |

-continued

|   |   |
|---|---|
| N-methylpyrrolidone | 50% |
| Solvesso 150 | 35% |

The first three components are dissolved in N-methylpyrrolidone and to this is then added the Solvesso 150 to give the final volume.

EXAMPLE 16-C

A wettable powder (WP) is prepared with the composition as follows:

|   |   |
|---|---|
| Active ingredient | 40% |
| Arylan S | 2% |
| Darvan No 2 | 5% |
| Celite PF | 53% |

The ingredients are mixed and ground in a hammer-mill to a powder with a particle size of less than 50 microns.

EXAMPLE 16-D

An aqueous-flowable formulation is prepared with the composition as follows:

|   |   |
|---|---|
| Active ingredient | 40.00% |
| Ethylan BCP | 1.00% |
| Sopropon T360. | 0.20% |
| Ethylene glycol | 5.00% |
| Rhodigel 230 | 0.15% |
| Water | 53.65% |

The ingredients are intimately mixed and are ground in a bead mill until a mean particle size of less than 3 microns is obtained.

EXAMPLE 16-E

An emulsifiable suspension concentrate is prepared with the composition as follows:

|   |   |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 16-F

A water dispersible granule is prepared with the composition as follows:

|   |   |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 16-G

A dusting powder is prepared with the composition as follows:

|   |   |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 16-H

An edible bait is prepared with the composition as follows:

|   |   |
|---|---|
| Active ingredient | 0.1 to 1.0% |
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 16-I

A solution formulation is prepared with a composition as follows:

|   |   |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 16-J

A wettable powder is prepared with the composition as follows:

|   |   |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 16-K

A slow release bolus composition is formed from granules containing the following components in varying percentages (similar to those described for the previous compositions) depending upon need:

| |
| --- |
| Active ingredient |
| Density agent |
| Slow-release agent |
| Binder |

The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 16-L

A slow release composition in the form of granules, pellets, brickettes or the like can be prepared with compositions as follows:

| | |
| --- | --- |
| Active ingredient | 0.5 to 25% |
| Polyvinyl chloride | 75 to 99.5% |
| Dioctyl phthalate (plasticizer) | |

The components are blended and then formed into suitable shapes by melt-extrusion or molding. These composition are useful, for example, for addition to standing water or for fabrication into collars or eartags for attachment to domestic animals to control pests by slow release.

While the invention has been described in terms of various preferred embodiments, the skilled artisan will appreciate that various modifications, substitutions, omissions and changes may be made without departing from the spirit thereof. Accordingly it is intended that the scope of the present invention be limited solely by the scope of the following claims, including equivalents thereof.

What is claimed is:
1. A compound having the formula:

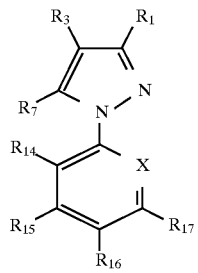

wherein:
$R_1$ is cyano, halogen, formyl, —$C(O)R_2$, H, or $R_2$;
$R_2$ is $C_1$–$C_4$ alkyl, $C_1$–$C_4$ haloalkyl, or cycloalkyl which is unsubstituted or is substituted with one or more halogen;
$R_3$ is —$S(O)_nR_6$;
$R_6$ is $C_1$–$C_4$ alkyl, $C_1$–$C_4$ haloalkyl, or cycloalkyl which is unsubstituted or is substituted with one or more halogen;
$R_7$ is —$C(O)R_8$
$R_8$ is H, $C_1$–$C_5$ alkyl, or $C_1$–$C_5$ haloalkyl;
$R_{14}$ is H, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, cyano or nitro;
$R_{15}$ and $R_{17}$ are, independently, H or halogen;
$R_{16}$ is halogen, $C_1$–$C_4$ alkyl, $C_1$–$C_4$ haloalkyl, $C_1$–$C_4$ alkoxy, $C_1$–$C_4$ haloalkoxy, cyano, nitro, —$C(O)R_{18}$, or $S(O)_qR_{19}$;
$R_{18}$ is $C_1$–$C_3$ alkyl or $C_1$–$C_3$ haloalkyl;
$R_{19}$ is $C_1$–$C_3$ alkyl or $C_1$–$C_3$ haloalkyl;
$R_{20}$ is H, halogen, cyano, nitro, $C_1$–$C_4$ alkyl, $C_1$–$C_4$ haloalkyl, $C_1$–$C_4$ alkoxy, or $C_1$–$C_4$ haloalkoxy;
X is a nitrogen atom or C—$R_{20}$,
n is 0, 1 of 2; and
q is 0, 1 or 2;
or a pesticidally acceptable salt thereof.

2. A compound according to claim 1 having at least one feature selected from the group consisting of:
 (a) $R_1$ is cyano;
 (b) $R_{14}$ is halogen;
 (c) each of $R_{15}$ and $R_{17}$ is H;
 (d) $R_{16}$ is $C_1$–$C_4$ haloalkyl; and
 (e) X is C—$R_{20}$.

3. A compound according to claim 1 wherein $R_1$ is cyano, halogen, —$C(O)R_2$, H, or $R_2$; $R_{14}$ is halogen; each of $R_{15}$ and $R_{17}$ is H; and $R_{16}$ is $C_1$–$C_4$ haloalkyl.

4. A compound according to claim 1 wherein $R_1$ is cyano; $R_6$ is $C_1$–$C_2$ haloalkyl; $R_{14}$ is halogen; each of $R_{15}$ and $R_{17}$ is H; and $R_{16}$ is $C_1$–$C_2$ haloalkyl.

5. A compound according to claim 2 wherein $R_1$ is cyano; $R_6$ is $C_1$–$C_2$ haloalkyl; $R_{14}$ is halogen; each of $R_{15}$ and $R_{17}$ is H; and $R_{16}$ is $C_1$–$C_2$ haloalkyl.

6. A compound according to claim 1 wherein $R_6$ is $CF_3$ and $R_{16}$ is $CF_3$.

7. A compound according to claim 2 wherein $R_6$ is $CF_3$ and $R_{16}$ is $CF_3$.

8. A compound according to claim 3 wherein $R_6$ is $CF_3$ and $R_{16}$ is $CF_3$.

9. A compound according to claim 4 wherein $R_6$ is $CF_3$ and $R_{16}$ is $CF_3$.

10. A compound according to claim 5 wherein $R_6$ is $CF_3$ and $R_{16}$ is $CF_3$.

11. The compound according to claim 1 which is:

5-acetyl-3-cyano-1-(2,6-dichloro-4-trifluoromethylphenyl)4-trifluoromethylsulfonylpyrazole;

3-cyano-1-(2,6-dichloro4-trifluoromethylphenyl)-5-formyl4-trifluoromethylthiopyrazole;

5-acetyl-3-cyano-1-(2,6-dichloro4-trifluoromethylphenyl)4-trifluoromethylthiopyrazole; or 5-acetyl-3-cyano-1-(2,6-dichloro4-trifluoromethylphenyl)-4-trifluoromethylsulfinylpyrazole.

12. A pesticidal composition comprising a pesticidally effective amount of a compound of formula (I) as defined in claim 1 or a pesticidally acceptable salt thereof, and a pesticidally acceptable carrier therefor.

13. A composition according to claim 12 further comprising a pesticidally acceptable surface-active agent.

14. A method for controlling pests at a locus comprising applying to said locus a pesticidally effective amount of a compound of formula (I) as defined in claim 1 or a pesticidally acceptable salt thereof.

15. A method according to claim 14 wherein said locus is an area used or to be used for the growing of crops.

16. A process for the preparation of a compound of formula (I) as defined in claim 1, said process comprising:

(a) oxidizing a compound corresponding to formula (I) as defined in claim 1 except that $R_7$ in said compound is $C_1$–$C_6$ α-hydroxyalkyl or $C_1$–$C_6$ α-halohydroxyalkyl, to afford the corresponding compound of formula (I) as defined in claim 1; or (b) subjecting to oxidative cleavage a compound of the formula:

wherein $R_{25}$ is ($C_1$–$C_{12}$ alkyl)carbonyl, ($C_1$–$C_{12}$ alkoxy)carbonyl, cyano or nitro, and Q is a group of the formula:

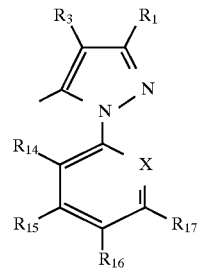

in which $R_1$, $R_3$, $R_{14}$, $R_{15}$, $R_{16}$ and $R_{17}$ and X are as defined in claim 1, to afford the corresponding compound of formula (I) wherein $R_7$ is formyl;

optionally followed by converting the compound thus obtained into a pesticidally acceptable salt thereof.

* * * * *